US005710015A

United States Patent [19]

McAllister et al.

[11] Patent Number: 5,710,015
[45] Date of Patent: Jan. 20, 1998

[54] CDNA CLONING OF INOSITOL MONOPHOSPHATASE

[75] Inventors: George McAllister, Bishops Stortford; Paul John Whiting, Stansted Mountfitchet, both of United Kingdom

[73] Assignee: Merck, Sharp & Dohme, Ltd., Hoddesdon, England

[21] Appl. No.: 347,471

[22] PCT Filed: May 25, 1993

[86] PCT No.: PCT/SE93/00457

§ 371 Date: Jan. 18, 1995

§ 102(e) Date: Jan. 18, 1995

[87] PCT Pub. No.: WO93/25692

PCT Pub. Date: Dec. 23, 1993

[30] Foreign Application Priority Data

Jun. 10, 1992 [GB] United Kingdom ............... 9212261

[51] Int. Cl.$^6$ ............... C12N 15/12; C12N 1/21; C12N 15/63; C12N 9/16
[52] U.S. Cl. ............... 435/69.1; 435/172.3; 435/252.3; 435/252.33; 435/325; 435/196; 530/350; 536/23.2
[58] Field of Search ............... 530/350; 435/4, 435/252.33, 252.3, 325, 172.3, 69.1, 196; 536/23.2

[56] References Cited

PUBLICATIONS

"Cloning and Expression of Bovine Brain Inositol Monophosphatase", Ronald E. Diehl, et al., Journal of Biological Chemistry, vol. 265, No. 11, Apr. 15, 1990, pp. 5946–5949.

"Purification and Properties of myo–Inositol–1–Phosphatase from Rat Brain", Kouichi Takimoto, Journal of Biochemistry, vol. 98, No. 2, 1985, pp. 363–370.

"cDNA cloning of human and rat brain myo–inositol monophosphatase", George McAllister, et al., The Biochemical Journal, vol. 284, No. 3, Jun. 15, 1992, pp. 749–754.

"Human brain 2'–nucleotidase: partial purification and properties", U. Vogel, et al., Biochemical Society Transactions, vol. 14, No. 2, Apr. 1986, pp. 349–350.

Primary Examiner—George C. Elliott
Assistant Examiner—Johnny F. Railey, II
Attorney, Agent, or Firm—Robert J. North; Melvin Winokur

[57] ABSTRACT

The present invention relates to the cloning of novel cDNA sequences encoding human and rat inositol monophosphatase (IMP); to the preparation of IMP enzyme by incorporation of the cDNAs into an expression vector and the expression thereof in recombinant host cells; and to the use of the enzyme thereby obtained in designing and developing medicaments which are inhibitors of human or rat IMP.

7 Claims, No Drawings

CDNA CLONING OF INOSITOL MONOPHOSPHATASE

The present invention relates to cDNA encoding inositol monophosphatase (IMP) which is isolated from brain cells. As used herein, the abbreviation IMP refers to an enzyme which can specifically liberate inositol (Ins) from the naturally occurring substrates Ins(1)P, Ins(3)P and Ins(4)P. IMP is also capable of hydrolyzing certain non-inositol-containing substrates including but not limited to those disclosed in Hallcher and Sherman, (1980), *J. Biol. Chem.*, 224, pp. 10896–10901; Takimoto et al., (1985), *J. Biochem* (Tokyo), 98, pp. 363–370; and Gee et al., (1988), *Biochem. J.*, 249, pp. 883–889.

The amino acid and cDNA sequence of bovine IMP is known [Diehl et al., (1989), *J. Biol. Chem.*, 265, pp. 5946–5949]. Mammalian cells capable of producing IMP include, but are not limited to, brain tissue cells. Transformed mammalian cell lines which may produce IMP include, but are not limited to, brain derived cell lines such as those available from the American Type Culture Collection listed in the *Catalogue of Cell lines & Hybridomas*, 7th Edition, 1992. The preferred cells for the present invention include normal human brain-derived tissue cells.

Other cells and cell lines may also be suitable for use in isolating IMP cDNA. Selection of suitable cells may be done by screening for IMP activity in cell extracts or conditioned medium. Methods for detecting IMP activity are well known in the art [Ragan et al., (1988), *Biochem. J.*, 249, pp. 143–148], and measure the liberation of $^{14}$C-labelled inositol from a substrate. Cells which possess IMP activity in this assay may be suitable for the isolation of IMP cDNA.

Any of a variety of procedures may be used to molecularly clone human IMP cDNA. These methods include, but are not limited to, direct functional expression of the human IMP cDNA following the construction of a human IMP containing cDNA library in an appropriate expression vector system. Another method is to screen a human IMP-containing cDNA library constructed in a bacteriophage or plasmid shuttle vector with a labelled oligonucleotide probe designed from the amino acid sequence of the purified IMP protein or from the DNA sequence of bovine IMP cDNA. The preferred method consists of screening a human IMP-containing cDNA library constructed in a bacteriophage or plasmid shuttle vector with a $^{32}$P-labelled cDNA oligonucleotide-primed fragment of the bovine IMP cDNA [Diehl et al., (1989), *J. Biol. Chem.*, 265, pp. 5946–5949]. The preferred cDNA library is a commercially available human hippocampal cDNA library in lambdaZAP (Stratagene).

It is readily apparent to those skilled in the art that other types of libraries, as well as libraries constructed from other cells or cell types, may be useful for isolating IMP-encoding DNA. Other types of libraries include, but are not limited to, cDNA libraries derived from other tissues, cells or cell lines other than human hippocampal cells, and genomic DNA libraries.

It is readily apparent to those skilled in the art that suitable cDNA libraries may be prepared from cells or cell lines which have IMP activity. The selection of cells or cell lines for use in preparing a cDNA library to isolate IMP cDNA may be done by first measuring cell-associated IMP activity using the $^{14}$C-labelled inositol substrate cleavage assay described above [Ragan et al., supra].

Preparation of cDNA libraries can be performed by standard techniques well known in the art. Well known cDNA library construction techniques can be found, for example, in Maniatis, T., Fritsch, E. F., Sambrook, J., *Molecular Cloning: A Laboratory Manual* (Cold Spring Harbor Press, New York, 2nd edition, 1989).

It is also readily apparent to those skilled in the art that DNA encoding IMP may also be isolated from a suitable genomic DNA library.

Construction of genomic DNA libraries can be performed by standard techniques well known in the art. Well known genomic DNA library construction techniques can be found in Maniatis et al., supra.

Using the preferred method, cDNA clones encoding human IMP were isolated by cDNA library screening. $^{32}$P-radiolabelled oligonucleotide-primed fragments of the bovine IMP cDNA served as probes for the isolation of full length human IMP cDNA from a commercially available lambdaZAP cDNA library (Stratagene) derived from human hippocampal cells.

Three positively hybridising phage, designated lambdaHIMP1-3, were detected using the bovine IMP cDNA-derived probe. These cDNA clones contained an insert of about 2 kilobases (kb) in length and had a single open reading frame of about 277 amino acids. Following in vivo excision according to the standard protocol as supplied by the manufacturer (Stratagene), three plasmids were obtained, designated pHIMP1-3 respectively. These positive cDNA clones were bi-directionally sequenced by the dideoxy chain termination method (Sanger et al., *P.N.A.S. USA*, 74, 5463, 1977).

The sequence (SEQ. ID NO. 1) for the full-length cDNA encoding human brain IMP is shown in Table 1, and was derived from clone pHIMP3. The deduced amino acid sequence (SEQ. ID NO. 2) of human IMP from the cloned cDNA is shown alongside the cDNA sequence in Table 1. Inspection of the cDNA sequence reveals the presence of a single, large open reading frame of 277 amino acids. A comparison of the bovine IMP amino acid sequence with the human IMP amino acid sequence shows about 85% sequence identity.

TABLE 1

| | | | | | | | | | | −1 | +1 | | | | | | |
|---|---|---|---|---|---|---|---|---|---|---|---|---|---|---|---|---|---|
| −36 | CTC | CGA | CTC | AAG | ATA | TTT | GTC | AAA | TAT | TTT | CAG | AAG | ATG | GCT | GAT | CCT | TGG | CAG |
| | | | | | | | | | | | | | M | A | D | P | W | Q | 6 |
| 19 | GAA | TGC | ATG | GAT | TAT | GCA | GTA | ACT | CTA | GCA | AGA | CAA | GCT | GGA | GAG | GTA | GTT | TGT |
| | E | C | M | D | Y | A | V | T | L | A | R | Q | A | G | E | V | V | C | 24 |
| 73 | GAA | GCT | ATA | AAA | AAT | GAA | ATG | AAT | GTT | ATG | CTG | AAA | AGT | TCT | CCA | GTT | GAT | TTG |
| | E | A | I | K | N | E | M | N | V | M | L | K | S | S | P | V | D | L | 42 |
| 127 | GTA | ACT | GCT | ACG | GAC | CAA | AAA | GTT | GAA | AAA | ATG | CTT | ATC | TCT | TCC | ATA | AAG | GAA |
| | V | T | A | T | D | Q | K | V | E | K | M | L | I | S | S | I | K | E | 60 |
| 181 | AAG | TAT | CCA | TCT | CAC | AGT | TTC | ATT | GGT | GAA | GAA | TCT | GTG | GCA | GCT | GGG | GAA | AAA |
| | K | Y | P | S | H | S | F | I | G | E | E | S | V | A | A | G | E | K | 78 |

TABLE 1-continued

| | | | | | | | | | | | | | | | | | | |
|---|---|---|---|---|---|---|---|---|---|---|---|---|---|---|---|---|---|---|
| 235 | AGT | ATC | TTA | ACC | GAC | AAC | CCC | ACA | TGG | ATC | ATT | GAC | CCT | ATT | GAT | GGA | ACA | ACT |
| | S | I | L | T | D | N | P | T | W | I | I | D | P | I | D | G | T | T | 96 |
| 289 | AAC | TTT | GTA | CAT | AGA | TTT | CCT | TTT | GTA | GCT | GTT | TCA | ATT | GGC | TTT | GCT | GTA | AAT |
| | N | F | V | H | R | F | P | F | V | A | V | S | I | G | F | A | V | N | 114 |
| 343 | AAA | AAG | ATA | GAA | TTT | GGA | GTT | GTG | TAC | AGT | TGT | GTG | GAA | GGC | AAG | ATG | TAC | ACT |
| | K | K | I | E | F | G | V | V | Y | S | C | V | E | G | K | M | Y | T | 132 |
| 397 | GCC | AGA | AAA | GGA | AAA | GGG | GCC | TTT | TGT | AAT | GGT | CAA | AAA | CTA | CAA | GTT | TCA | CAA |
| | A | R | K | G | K | G | A | F | C | N | G | Q | K | L | Q | V | S | Q | 150 |
| 451 | CAA | GAA | GAT | ATT | ACC | AAA | TCT | CTC | TTG | GTG | ACT | GAG | TTG | GGC | TCT | TCT | AGA | ACA |
| | Q | E | D | I | T | K | S | L | L | V | T | E | L | G | S | S | R | T | 168 |
| 505 | CCA | GAG | ACT | GTG | AGA | ATG | GTT | CTT | TCT | AAT | ATG | GAA | AAG | CTT | TTT | TGC | ATT | CCT |
| | P | E | T | V | R | M | V | L | S | N | M | E | K | L | F | C | I | P | 186 |
| 559 | GTT | CAT | GGG | ATC | CGG | AGT | GTT | GGA | ACA | GCA | GCT | GTT | AAT | ATG | TGC | CTT | GTG | GCA |
| | V | H | G | I | R | S | V | G | T | A | A | V | N | M | C | L | V | A | 204 |
| 613 | ACT | GGC | GGA | GCA | GAT | GCA | TAT | TAT | GAA | ATG | GGA | ATT | CAC | TGC | TGG | GAT | GTT | GCA |
| | T | G | G | A | D | A | Y | Y | E | M | G | I | H | C | W | D | V | A | 222 |
| 667 | GGA | GCT | GGC | ATT | ATT | GTT | ACT | GAA | GCT | GGT | GGC | GTG | CTA | ATG | GAT | GTT | ACA | GGT |
| | G | A | G | I | I | V | T | E | A | G | G | V | L | M | D | V | T | G | 240 |
| 721 | GGA | CCA | TTT | GAT | TTG | ATG | TCA | CGA | AGA | GTA | ATT | GCT | GCA | AAT | AAT | AGA | ATA | TTA |
| | G | P | F | D | L | M | S | R | R | V | I | A | A | N | N | R | I | L | 258 |
| 775 | GCA | GAA | AGG | ATA | GCT | AAA | GAA | ATT | CAG | GTT | ATA | CCT | TTG | CAA | CGA | GAC | GAC | GAA |
| | A | E | R | I | A | K | E | I | Q | V | I | P | L | Q | R | D | D | E | 276 |
| 829 | GAT | TAA | TTA | AGG | CAG | CTC | ATA | GTC | ATC | CAG | TTG |
| | D | END |

In addition to the isolation and cloning of human brain IMP cDNA, rat brain IMP cDNA was also isolated and cloned from a cDNA library. A commercially available rat brain cDNA library (Clontech) constructed in lambdaGT11 was screened using $^{32}$P-radiolabelled oligonucleotide-primed fragments of the bovine IMP cDNA as probes. Plaques were plated and two positive clones were identified. Both clones contained DNA inserts of approximately 2.1 kb which were sequenced. The DNA inserts were identical and contained an open reading frame of 270 amino acids beginning from amino acid residue 8 of the human brain IMP DNA sequence (cf. Table 1). The sequence of this cDNA insert, together with the deduced amino acid sequence (SEQ. ID NO. 4) corresponding thereto, is shown in Table 2.

TABLE 2

| | | | | | | | | 27 | | | | | | | | | 54 |
|---|---|---|---|---|---|---|---|---|---|---|---|---|---|---|---|---|---|
| TGC | ATG | GAT | TAT | GCA | GTG | ATC | CTC | GCA | AGA | CAA | GCT | GGA | GAG | ATG | ATT | CGA | GTT |
| C | M | D | Y | A | V | I | L | A | R | Q | A | G | E | M | I | R | V |
| | | | | | | | | 81 | | | | | | | | | 108 |
| GCT | CTA | AAA | AAT | AAG | ATG | GAT | GTC | ATG | ATT | AAA | AGT | TCT | CCA | GCC | GAC | TTG | GTA |
| A | L | K | N | K | M | D | V | M | I | K | S | S | P | A | D | L | V |
| | | | | | | | | 135 | | | | | | | | | 162 |
| ACA | GTT | ACT | GAC | CAA | AAA | GTT | GAA | AAA | ATG | CTT | ATG | TCT | TCT | ATA | AAG | GAA | AAA |
| T | V | T | D | Q | K | V | E | K | M | L | M | S | S | I | K | E | K |
| | | | | | | | | 189 | | | | | | | | | 216 |
| TAC | CCA | TAT | CAC | AGT | TTC | ATT | GGT | GAA | GAA | TCT | GTG | GCA | GCC | GGG | GAA | AAG | ACA |
| Y | P | Y | H | S | F | I | G | E | E | S | V | A | A | G | E | K | T |
| | | | | | | | | 243 | | | | | | | | | 270 |
| GTC | TTC | ACA | GAG | CAG | CCC | ACG | TGG | ATC | ATT | GAT | CCC | ATT | GAC | GGG | ACG | ACC | AAC |
| V | F | T | E | Q | P | T | W | I | I | D | P | I | D | G | T | T | N |
| | | | | | | | | 297 | | | | | | | | | 324 |
| TTT | GTG | CAC | CGG | TTT | CCC | TTT | GTA | GCT | GTT | TCG | ATT | GGC | TTC | GTT | GTA | AAT | AAA |
| F | V | H | R | F | P | F | V | A | V | S | I | G | F | V | V | N | K |
| | | | | | | | | 351 | | | | | | | | | 378 |
| GAG | ATG | GAG | TTT | GGA | GTT | GTA | TAC | AGC | TGT | GTG | GAA | GAT | AAG | ATG | TAT | ACG | GGC |
| E | M | E | F | G | V | V | Y | S | C | V | E | D | K | M | Y | T | G |
| | | | | | | | | 405 | | | | | | | | | 432 |
| AGG | AAA | GGA | AAA | GGC | GCC | TTT | TGT | AAC | GGT | CAG | AAG | CTT | CGG | GTC | TCG | CAG | CAG |
| R | K | G | K | G | A | F | C | N | G | Q | K | L | R | V | S | Q | Q |
| | | | | | | | | 459 | | | | | | | | | 486 |
| GAA | GAC | ATT | ACC | AAA | TCA | CTC | TTG | GTG | ACC | GAG | CTG | GGA | TCG | TCC | AGA | AAG | CCG |
| E | D | I | T | K | S | L | L | V | T | E | L | G | S | S | R | K | P |
| | | | | | | | | 513 | | | | | | | | | 540 |
| GAG | ACT | TTG | CGG | ATT | GTT | CTC | TCC | AAC | ATG | GAA | AGG | CTT | TGC | TCC | ATT | CCT | ATC |
| E | T | L | R | I | V | L | S | N | M | E | R | L | C | S | I | P | I |
| | | | | | | | | 567 | | | | | | | | | 594 |
| CAT | GGA | ATC | CGG | AGT | GTT | GGG | ACA | GCG | GCT | GTT | AAT | ATG | TGC | CTT | GTG | GCA | ACG |
| H | G | I | R | S | V | G | T | A | A | V | N | M | C | L | V | A | T |
| | | | | | | | | 621 | | | | | | | | | 648 |
| GGA | GGA | GCG | GAT | GCC | TAT | TAC | GAG | ATG | GGG | ATC | CAC | TGC | TGG | GAC | ATG | GCT | GGA |
| G | G | A | D | A | Y | Y | E | M | G | I | H | C | W | D | M | A | G |
| | | | | | | | | 675 | | | | | | | | | 702 |
| GCT | GGC | ATC | ATC | GTC | ATA | GAG | GCT | GGC | GGA | GTG | CTG | CTG | GAT | GTG | ACA | GGT | GGA |
| A | G | I | I | V | I | E | A | G | G | V | L | L | D | V | T | G | G |
| | | | | | | | | 729 | | | | | | | | | 756 |
| CCA | TTC | GAT | TTG | ATG | TCT | CGG | AGA | ATA | ATT | GCT | GCA | AGT | AAT | ATA | GCA | TTA | GCA |
| P | F | D | L | M | S | R | R | I | I | A | A | S | N | I | A | L | A |

TABLE 2-continued

|  |  |  |  |  |  |  |  | 783 |  |  |  |  |  |  |  | 810 |
|---|---|---|---|---|---|---|---|---|---|---|---|---|---|---|---|---|
| GAA | AGA | ATA | GCC | AAA | GAA | CTT | GAG | ATA | ATA | CCT | TTA | CAA | CGA | GAC | GAC | GAA | AGT |
| E | R | I | A | K | E | L | E | I | I | P | L | Q | R | D | D | E | S |
|  |  |  |  |  |  |  |  | 837 |  |  |  |  |  |  |  | 864 |
| TAG | GCA | CGT | AGA | ACC | GCA | TCC | AGC | TCC | GTC | ACA | CCT | GCT | CTC | CCT | GGG | ATG | TTT |
| End |
|  |  |  |  |  |  | 891 |
| AAA | GAT | GTA | TGA | TGT | CAC | TGA | TTT | AAA | TTT | AAC | TTT | GCA | GTC | CTG |

IMP in substantially pure form derived from natural sources is found to be an association of two IMP polypeptides apparently encoded by a single mRNA [Gee et al., Biochem. J., 1988, 549, 883–889]. The two IMP polypeptides are found to have an apparent molecular weight of about 30 kDa.

The cloned IMP cDNA obtained through the methods described above may be recombinantly expressed by molecular cloning into an expression vector containing a suitable promoter and other appropriate transcription regulatory elements, and then transferring the expression vector into prokaryotic or eukaryotic host cells to produce recombinant IMP. Molecular cloning of cDNAs into an expression vector can be achieved by a variety of standard techniques; in the present context, polymerase chain reaction (PCR) methodology [Saiki et al., Science, 1988, 239, 487–491] is preferably employed. Alternative conventional techniques for such manipulations are fully described in Maniatis et al., supra, and are well known in the art.

Expression vectors are defined herein as DNA sequences that are required for the transcription of cloned copies of genes and the translation of their mRNAs in an appropriate host. Such vectors can be used to express eukaryotic genes in a variety of hosts such as bacteria, bluegreen algae, plant cells, insect cells and animal cells.

Specifically designed vectors allow the shuttling of DNA between hosts such as bacteria-yeast or bacteria-animal cells. An appropriately constructed expression vector should contain: an origin of replication for autonomous replication in host cells, selectable markers, a limited number of useful restriction enzyme sites, a potential for high copy number, and active promoters. A promoter is defined as a DNA sequence that directs RNA polymerase to bind to DNA and initiate RNA synthesis. A strong promoter is one which causes mRNAs to be initiated at high frequency. Expression vectors may include, but are not limited to, cloning vectors, modified cloning vectors, specifically designed plasmids or viruses.

A variety of mammalian expression vectors may be used to express recombinant IMP in mammalian cells. Commercially available mammalian expression vectors which may be suitable for recombinant IMP expression include, but are not limited to, pRSET5a [Schoepfer et al., FEBS Lett., 1990, 257, 393–399], pMClneo (Stratagene), pXT1 (Stratagene), pSG5 (Stratagene), EBO-pSV2-neo (ATCC 37593), pBPV-1(8-2) (ATCC 37110), pdBPV-MMTneo (342-12) (ATCC 37224), pRSVgpt (ATCC 37199), pRSVneo (ATCC 37198), pSV2-dhfr (ATCC 37146), pUCTag (ATCC 37460), and gZD35 (ATCC 37565).

DNA encoding IMP cloned into an expression vector may then be transferred to a recombinant host cell for expression. Recombinant host cells may be prokaryotic or eukaryotic, including but not limited to bacteria, yeast, mammalian cells (including but not limited to cell lines of human, bovine, porcine, monkey and rodent origin), and insect cells (including but not limited to drosophila derived cell lines). A preferred bacterial cell line is BL21-DE3 [Schoepfer et al., FEBS Lett., 1990, 257, 393–399]. Cell lines derived from mammalian species which may be suitable and which are commercially available include, but are not limited to, CV-1 (ATCC CCL 70), COS-1 (ATCC CRL 1650), COS-7 (ATCC CRL 1651), CHO-K1 (ATCC CCL 61), 3T3 (ATCC CCL 92), NIH/3T3 (ATCC CRL 1658), HeLa (ATCC CCL 2), C127I (ATCC CRL 1616), BS-C-1 (ATCC CCL 26) and MRC-5 (ATCC CCL 171).

It will be appreciated that, if the cDNA is to be inserted into the expression vector pRSET5a, then this expression vector must be used in conjunction with a recombinant host containing the T7 polymerase gene. One such host is the bacterial strain BL21-DE3. Thus, a preferred method in the present case is to insert the cDNA into the expression vector pRSET5a and express this vector in the bacterial strain BL21-DE3.

The expression vector may be introduced into host cells via any one of a number of techniques including but not limited to transformation, transfection, protoplast fusion, and electroporation. The expression vector-containing cells are clonally propagated and individually analyzed to determine whether they produce IMP protein. Identification of IMP expressing host cell clones may be done by several means, including but not limited to immunological reactivity with anti-IMP antibodies, and the presence of host cell-associated IMP activity.

Expression of IMP DNA may also be performed using in vitro produced synthetic mRNA. Synthetic mRNA can be efficiently translated in various cell-free systems, including but not limited to wheat germ extracts and reticulocyte extracts, as well as efficiently translated in cell based systems, including but not limited to microinjection into frog oocytes.

To determine the IMP cDNA sequence(s) that yield(s) optimal levels of enzymatic activity and/or IMP protein, IMP cDNA molecules including but not limited to the following can be constructed: the full-length open reading frame of the IMP cDNA (base 1 to base 834; Table 1) and constructs containing portions of the cDNA encoding enzymatically active protein. All constructs can be designed to contain none, all or portions of the 5' and 3' untranslated region of IMP cDNA. A particular construct is one which is substantially free of the 5' untranslated region of IMP cDNA. IMP activity and levels of protein expression can be determined following the introduction, both singly and in combination, of these constructs into appropriate host cells. Following determination of the IMP cDNA cassette which yields optimal expression, this IMP cDNA construct may be transferred to a variety of expression host cells, including but not limited to mammalian cells, baculovirus-infected insect cells, E. coli, and the yeast S. cerevisiae.

Expression of IMP in a recombinant host cell affords IMP protein in active form, capable of enzymatically liberating inositol from naturally occurring IMP substrates. Several IMP purification procedures are available and suitable for use. Recombinant IMP may be purified from cell lysates and extracts, or from conditioned culture medium, by various combinations of, or individual application of, salt fractionation, ion exchange chromatography, size exclusion chromatography, hydroxylapatite adsorption chromatography and hydrophobic interaction chromatography. The preferred method is ion-exchange chromatography utilizing a column of HR5/5 Mono Q matrix (LKB Pharmacia).

In addition, recombinant IMP can be separated from other cellular proteins by use of an immuno-affinity column made with monoclonal or polyclonal antibodies specific for IMP, or polypeptide fragments of IMP. The preparation and purification of monoclonal or polyclonal antibodies specific for IMP or polypeptide fragments thereof can be accomplished by conventional techniques well known in the art. Typical procedures include those described, for example, by Maniatis et al. in *Molecular Cloning, A Laboratory Manual*, Cold Spring Harbor Press, 2nd edition, 1989, Chapter 18.

This invention provides an antisense oligonucleotide having a sequence capable of binding specifically with any sequences of an mRNA molecule which encodes IMP, preferably human IMP, so as to prevent translation of the mRNA molecule. The antisense oligonucleotide may have a sequence capable of binding specifically with any sequences of the cDNA molecule whose sequence is shown in Table 1 or the cDNA molecule whose sequence is shown in Table 2. A particular example of an antisense oligonucleotide is an antisense oligonucleotide comprising chemical analogues of nucleotides.

This invention provides a transgenic nonhuman mammal expressing DNA encoding IMP, preferably human IMP. This invention also provides a transgenic nonhuman mammal expressing DNA encoding IMP, preferably human IMP, so mutated as to be incapable of normal receptor activity, and not expressing native IMP. This invention further provides a transgenic nonhuman mammal whose genome comprises antisense DNA complementary to DNA encoding IMP, preferably human IMP, so placed as to be transcribed into antisense mRNA which is complementary to mRNA encoding IMP and which hybridizes to mRNA encoding IMP thereby reducing its translation. The DNA may additionally comprise an inducible promoter or additionally comprise tissue specific regulatory elements, so that expression can be induced, or restricted to specific cell types. Examples of DNA are DNA or cDNA molecules having a coding sequence substantially the same as the coding sequence shown in Table 1, or the coding sequence shown in Table 2. An example of a transgenic animal is a transgenic mouse. Examples of tissue specificity-determining regions are the metallothionein promotor (Low et al., *Science*, 1986, 231, 1002–1004) and the L7 promotor (Oberdick et al., *Science*, 1990, 248, 223–226).

The cloned IMP enzyme in accordance with the invention, when isolated, may be utilised to generate structural data, in particular X-ray crystallographic data. Knowledge of, for example, the X-ray crystal structure of the IMP enzyme, especially human IMP, may facilitate in designing drugs which are inhibitors of this enzyme. The present invention accordingly provides the use of the cloned IMP enzyme in screening for and designing medicaments which are inhibitors of IMP.

The following non-limiting Examples illustrate the present invention.

EXAMPLE 1

Cloning of Human and Rat Brain Inositol Monophosphatase

A human hippocampal cDNA library constructed in lambdaZAP (Stratagene) was screened using a $^{32}$P-radiolabelled oligonucleotide-primed fragment of bovine inositol monophosphatase cDNA as a probe [Diehl et al., (1990), *J. Biol. Chem.*, 265, pp. 5946–5949]. Phage (100,000) were plated and three independent cDNA clones were isolated. All three contained an insert of approximately 2 kb which were subsequently shown to have identical sequences. One of these clones was characterized further and found to contain a 277 amino acid open reading frame (Table 1). The predicted amino acid sequence (Table 1) is very similar to that of the bovine enzyme and has an estimated subunit $M_r$ of approximately 30,000, as does the bovine enzyme [Gee et al., (1988), *Biochem. J.*, 249, pp. 883–889].

Additionally, a rat brain cDNA library constructed in lambdaGT11 (Clontech) was screened using $^{32}$P-radiolabelled oligonucleotide-primed fragments of bovine inositol monophosphatase cDNA as a probe as described above. Phage were plated and two independent cDNA clones were isolated. Each contained an insert of approximately 2.1 kb which were subsequently shown to have identical sequences. One clone was characterized further and found to contain a 270 amino acid open reading frame beginning with amino acid 8 of the human brain IMP cDNA. The rat brain IMP cDNA sequence, together with the deduced amino acid sequence corresponding thereto, is shown in Table 2.

EXAMPLE 2

Expression of Recombinant Human Inositol Monophosphatase in Bacteria

The T7 polymerase bacterial expression system (pRSET5a) was used as described previously [Diehl et al., supra]. The coding region of the human inositol monophosphatase cDNA was reconstructed to contain an NdeI site at the start codon and a PstI site just downstream of the stop codon using PCR methodology [Saiki et al., (1988), *Science*, 239, pp. 487–491]. Oligonucleotides (SEQ. ID NO. 5) 5'-AATATTTTCAGCATATGGCTGATCCTTG-3' and (SEQ. ID NO. 6) 5'-ATGACTATGAGCTGCAGTAATTAATCTTC-3' were synthesized on an Applied Biosystems 380B instrument. Inositol monophosphatase cDNA (100 ng) in pBluescript II SK (Stratagene Ltd., U.K.) was subjected to PCR under standard conditions [Saiki, et al., supra], denaturation at 94° C. for 2 minutes, annealing at 55° C. for 2 minutes and polymerisation at 72° C. for 6 minutes. Twenty cycles were performed with the last polymerisation step lasting 12 minutes. The NdeI/PstI-digested PCR product was cloned into NdeI-PstI-digested pRSET5a and transformed into *Escherichia coli* strain DH5α competent cells. Positive clones were identified by restriction analysis and DNA sequencing. For subsequent expression studies, the expression vector was transformed into competent BL21-DE3 cells. Bacterial cells containing the expression vector were induced by isopropylthio-β-D-galactoside and analysed by both SDS/PAGE and enzyme assay.

Recombinant bacteria expressed a prominent polypeptide of about $M_r$ 30,000 which was absent from bacteria not containing the expression vector. Bacterial lysates contained significant amounts of enzyme activity, which was further purified by heat treatment, centrifugation and ion-exchange chromatography (Example 3).

EXAMPLE 3

Purification of Recombinant Human Inositol Monophosphatase

*E. coli* bacteria (strain BL21-DE3) containing the IMP expression vector (Example 2) were grown and induced by isopropylthio-β-D-galactoside, and analysed by SDS/PAGE and enzyme assay as described previously [Ragan et al., supra]. After induction, cells were pelleted and frozen until required for purification. THe bacterial pellets (1–2 g/liter of fermentation mixture) were thawed, resuspended in 10 volumes of 20 mM-TRIS/HCl/1 mM-EGTA buffer, pH 7.8 (buffer A) and sonicated on ice (3×1 min). The homogenate was then centrifuged at 100,000 xg for 20 minutes and the resultant supernatant was loaded, at a flow rate of 1 ml/min, on an HR5/5 Mono Q column (LKB Pharmacia), previously equilibrated with buffer A. The column was eluted at 1 ml/min with a gradient of 0–300 mM NaCl in buffer A, and 1 ml fractions were collected. Portions (5 µl) of each fraction were subjected to SDS/PAGE on 12% gels according to the method of Laemmli, (1970), *Nature*, 227, pp. 680–685. Gels were stained with Coomassie Blue and the appropriate inositol monophosphatase-containing fractions were pooled for subsequent analysis.

SDS/PAGE of a typical purification shows a single band of about $M_r$ 30,000. Table 3 shows a 5.4-fold purification of the enzyme, demonstrating that recombinant inositol monophosphatase constituted nearly 20% of the original bacterial protein. This level of expression enables the isolation of large amounts of pure enzyme for X-ray crystallography and other studies. The biochemical properties of the human enzyme were further examined.

TABLE 3

| Step | Total activity (m units) | Total protein (mg) | Specific activity (m units/mg) | Yield (%) |
|---|---|---|---|---|
| Bacterial homogenate | 751,100 | 214 | 3500 | 100 |
| Bacterial supernatant | 481,000 | 90 | 5300 | 64 |
| Heat-treated supernatant | 264,000 | 22 | 12,000 | 35 |
| Mono Q | 177,000 | 9 | 19,700 | 24 |

EXAMPLE 4

Kinetic Properties of Recombinant Human Inositol Monophosphatase

In agreement with previous work on the rat and bovine enzyme [Takimoto et al., (1985), *J. Biochem.*, 18, pp. 363–370; Gee et al., supra] we found that human brain IMP activity was totally dependent on $Mg^{2+}$. Under standard assay conditions, the apparent affinity of the human enzyme for $Mg^{2+}$ was approximately 2-fold greater than that of the bovine enzyme, and the human enzyme was also more sensitive to inhibition by high $Mg^{2+}$ concentrations. In the absence of KCl, activation by $Mg^{2+}$ occurred at approximately 2-fold lower concentrations, but maximum enzyme activity was independent of KCl. As is shown in Table 4, the recombinant human brain enzyme has similar kinetic properties to the native human platelet-derived enzyme as well as both the native and recombinant bovine enzymes [Gee et al., supra; Diehl et al., supra]. The $K_m$ for DL-Ins(1)P was lower for the human enzyme, suggesting that it may have a higher affinity for substrate than the bovine enzyme. These data also suggest that there is no significant post-translational modification of the native human enzyme that might change its behaviour compared with the recombinant enzyme.

TABLE 4

Kinetic properties of Inositol monophosphatases

| Enzyme | $K_m$ for DL-Ins(1)P (mM) | $V_{max}$ (µmol/min per mg of protein) |
|---|---|---|
| Human recombinant | 0.075 ± 0.003 | 36.8 ± 1 |
| Human platelet | 0.108 ± 0.003 | ND |
| Bovine recombinant | 0.12 ± 0.007 | ND |
| Bovine brain | 0.16 ± 0.02 | 13.3 ± 0.9 |

Initial rates determined with several substrate concentrations were fitted to a Michaelis-Menten expression by non-linear least-squares regression analysis. Values for $K_m$ and $V_{max}$ were determined in the present study and are given as means ±S.E.M. (n=3). Bovine brain values are as reported in Gee et al., supra, but confirmed here.

EXAMPLE 5

Inhibition of Recombinant Human Inositol Monophosphatase $P_i$ inhibited recombinant human IMP competitively with a $K_i$ value of 0.14 mM (cf. bovine enzyme, 0.5 mM), and $Li^+$ was an uncompetitive inhibitor with an apparent $K_i$ value of 0.3 mM (cf. bovine enzyme 0.26 mM). The competitive inhibitor 1S-phosphoryloxy-2R,4S-dihydroxycyclohexane [Baker et al., (1990), *J. Chem. Soc. Chem. Comm.*, pp. 462–464] inhibited with an apparent $K_i$ value of 2.7 µM (cf. bovine enzyme, 1.1 µM). All comparisons are from data obtained in parallel experiments carried out in this study. Overall, these data confirm that the human enzyme is similar to, but not identical with, the bovine enzyme. The availability of multiple protein sequences and recombinant human enzyme will assist future studies using site-directed mutagenesis and chemical-modification techniques to characterize important residues for the structure and function of this enzyme.

IMP Enzyme Assays

Enzyme activity was determined by measuring the release of [$^{14}$C]inositol from DL-Ins(1)P containing L-[U-$^{14}$C]Ins (1)P as label as described previously [Gumber et al., (1989), *Plant Physiol.*, 76, pp. 40–44]. One unit of enzyme activity represents 1 µmol of substrate hydrolysed/min, at 37° C. Protein concentrations were determined by the method of Bradford [Bradford, M., (1976), *Anal. Biochem.*, 72, pp. 248–252]. Kinetic analyses were performed as described previously [Gee et al., supra].

We claim:

1. A DNA molecule encoding the human inositol monophosphatase corresponding to the amino acid sequence depicted in SEQ. ID NO. 2 herein.

2. A DNA molecule corresponding to the nucleotide sequence depicted in SEQ ID NO. 1.

3. A recombinant expression vector comprising the nucleotide sequence as claimed in claim 1 together with additional sequences capable of directing the synthesis of inositol monophosphatase.

4. A recombinant host cell containing the expression vector as claimed in claim 3.

5. A host cell as claimed in claim 4 which consists of the bacterial cell line BL21-DE3 containing the recombinant expression vector pRSET5a.

6. A process for preparing recombinant inositol monophosphatase which comprises inserting the nucleotide sequence as claimed in claim 1 into an expression vector, incorporating the vector into a suitable host cell, and growing the host cell under conditions suitable for the expression of inositol monophosphatase.

7. A protein exhibiting human inositol monophosphatase activity and corresponding to the amino acid sequence depicted in SEQ. ID NO. 2 herein.

* * * * *

SEQUENCE LISTING ( 1 ) GENERAL INFORMATION:

( i i i ) NUMBER OF SEQUENCES: 6

( 2 ) INFORMATION FOR SEQ ID NO: 1:

( i ) SEQUENCE CHARACTERISTICS:
( A ) LENGTH: 897 base pairs
( B ) TYPE: nucleic acid
( C ) STRANDEDNESS: single
( D ) TOPOLOGY: linear ( i i ) MOLECULE TYPE: cDNA ( i x ) FEATURE:
( A ) NAME/KEY: CDS
( B ) LOCATION: 37..871

( x i ) SEQUENCE DESCRIPTION: SEQ ID NO: 1:

```
CTCCGACTCA AGATATTTGT CAAATATTTT CAGAAG ATG GCT GAT CCT TGG CAG       54
                                        Met Ala Asp Pro Trp Gln
                                         1               5

GAA TGC ATG GAT TAT GCA GTA ACT CTA GCA AGA CAA GCT GGA GAG GTA      102
Glu Cys Met Asp Tyr Ala Val Thr Leu Ala Arg Gln Ala Gly Glu Val
             10                  15                  20

GTT TGT GAA GCT ATA AAA AAT GAA ATG AAT GTT ATG CTG AAA AGT TCT      150
Val Cys Glu Ala Ile Lys Asn Glu Met Asn Val Met Leu Lys Ser Ser
         25                  30                  35

CCA GTT GAT TTG GTA ACT GCT ACG GAC CAA AAA GTT GAA AAA ATG CTT      198
Pro Val Asp Leu Val Thr Ala Thr Asp Gln Lys Val Glu Lys Met Leu
     40                  45                  50

ATC TCT TCC ATA AAG GAA AAG TAT CCA TCT CAC AGT TTC ATT GGT GAA      246
Ile Ser Ser Ile Lys Glu Lys Tyr Pro Ser His Ser Phe Ile Gly Glu
 55                  60                  65                  70

GAA TCT GTG GCA GCT GGG GAA AAA AGT ATC TTA ACC GAC AAC CCC ACA      294
Glu Ser Val Ala Ala Gly Glu Lys Ser Ile Leu Thr Asp Asn Pro Thr
                 75                  80                  85

TGG ATC ATT GAC CCT ATT GAT GGA ACA ACT AAC TTT GTA CAT AGA TTT      342
Trp Ile Ile Asp Pro Ile Asp Gly Thr Thr Asn Phe Val His Arg Phe
             90                  95                 100

CCT TTT GTA GCT GTT TCA ATT GGC TTT GCT GTA AAT AAA AAG ATA GAA      390
Pro Phe Val Ala Val Ser Ile Gly Phe Ala Val Asn Lys Lys Ile Glu
            105                 110                 115

TTT GGA GTT GTG TAC AGT TGT GTG GAA GGC AAG ATG TAC ACT GCC AGA      438
Phe Gly Val Val Tyr Ser Cys Val Glu Gly Lys Met Tyr Thr Ala Arg
        120                 125                 130

AAA GGA AAA GGG GCC TTT TGT AAT GGT CAA AAA CTA CAA GTT TCA CAA      486
Lys Gly Lys Gly Ala Phe Cys Asn Gly Gln Lys Leu Gln Val Ser Gln
135                 140                 145                 150

CAA GAA GAT ATT ACC AAA TCT CTC TTG GTG ACT GAG TTG GGC TCT TCT      534
Gln Glu Asp Ile Thr Lys Ser Leu Leu Val Thr Glu Leu Gly Ser Ser
                155                 160                 165

AGA ACA CCA GAG ACT GTG AGA ATG GTT CTT TCT AAT ATG GAA AAG CTT      582
Arg Thr Pro Glu Thr Val Arg Met Val Leu Ser Asn Met Glu Lys Leu
            170                 175                 180

TTT TGC ATT CCT GTT CAT GGG ATC CGG AGT GTT GGA ACA GCA GCT GTT      630
Phe Cys Ile Pro Val His Gly Ile Arg Ser Val Gly Thr Ala Ala Val
        185                 190                 195

AAT ATG TGC CTT GTG GCA ACT GGC GGA GCA GAT GCA TAT TAT GAA ATG      678
Asn Met Cys Leu Val Ala Thr Gly Gly Ala Asp Ala Tyr Tyr Glu Met
Ala Met Cys Leu Val Ala Thr Gly Gly Ala Asp Ala Tyr Tyr Glu Met
        200                 205                 210
```

-continued

```
GGA ATT CAC TGC TGG GAT GTT GCA GGA GCT GGC ATT ATT GTT ACT GAA         726
Gly Ile His Cys Trp Asp Val Ala Gly Ala Gly Ile Ile Val Thr Glu
215             220             225             230

GCT GGT GGC GTG CTA ATG GAT GTT ACA GGT GGA CCA TTT GAT TTG ATG         774
Ala Gly Gly Val Leu Met Asp Val Thr Gly Gly Pro Phe Asp Leu Met
                235             240             245

TCA CGA AGA GTA ATT GCT GCA AAT AAT AGA ATA TTA GCA GAA AGG ATA         822
Ser Arg Arg Val Ile Ala Ala Asn Asn Arg Ile Leu Ala Glu Arg Ile
            250             255             260

GCT AAA GAA ATT CAG GTT ATA CCT TTG CAA CGA GAC GAC GAA GAT TAA T       871
Ala Lys Glu Ile Gln Val Ile Pro Leu Gln Arg Asp Asp Glu Asp *
        265             270             275

TAAGGCAGCT CATAGTCATC CAGTTG                                             897
```

( 2 ) INFORMATION FOR SEQ ID NO: 2:

( i ) SEQUENCE CHARACTERISTICS:
        ( A ) LENGTH: 277 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 2:

```
Met Ala Asp Pro Trp Gln Glu Cys Met Asp Tyr Ala Val Thr Leu Ala
 1               5                  10                  15

Arg Gln Ala Gly Glu Val Val Cys Glu Ala Ile Lys Asn Glu Met Asn
            20                  25                  30

Val Met Leu Lys Ser Ser Pro Val Asp Leu Val Thr Ala Thr Asp Gln
        35                  40                  45

Lys Val Glu Lys Met Leu Ile Ser Ser Ile Lys Glu Lys Tyr Pro Ser
    50                  55                  60

His Ser Phe Ile Gly Glu Glu Ser Val Ala Ala Gly Glu Lys Ser Ile
65                  70                  75                  80

Leu Thr Asp Asn Pro Thr Trp Ile Ile Asp Pro Ile Asp Gly Thr Thr
                85                  90                  95

Asn Phe Val His Arg Phe Pro Phe Val Ala Val Ser Ile Gly Phe Ala
               100                 105                 110

Val Asn Lys Lys Ile Glu Phe Gly Val Val Tyr Ser Cys Val Glu Gly
        115                 120                 125

Lys Met Tyr Thr Ala Arg Lys Gly Lys Gly Ala Phe Cys Asn Gly Gln
    130                 135                 140

Lys Leu Gln Val Ser Gln Gln Glu Asp Ile Thr Lys Ser Leu Leu Val
145                 150                 155                 160

Thr Glu Leu Gly Ser Ser Arg Thr Pro Glu Thr Val Arg Met Val Leu
                165                 170                 175

Ser Asn Met Glu Lys Leu Phe Cys Ile Pro Val His Gly Ile Arg Ser
            180                 185                 190

Val Gly Thr Ala Ala Val Asn Met Cys Leu Val Ala Thr Gly Gly Ala
        195                 200                 205

Asp Ala Tyr Tyr Glu Met Gly Ile His Cys Trp Asp Val Ala Gly Ala
    210                 215                 220

Gly Ile Ile Val Thr Glu Ala Gly Gly Val Leu Met Asp Val Thr Gly
225                 230                 235                 240

Gly Pro Phe Asp Leu Met Ser Arg Arg Val Ile Ala Ala Asn Asn Arg
                245                 250                 255

Ile Leu Ala Glu Arg Ile Ala Lys Glu Ile Gln Val Ile Pro Leu Gln
            260                 265                 270
```

Arg Asp Asp Glu Asp
    275

(2) INFORMATION FOR SEQ ID NO: 3:

(i) SEQUENCE CHARACTERISTICS:
        (A) LENGTH: 909 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..813

(xi) SEQUENCE DESCRIPTION: SEQ ID NO: 3:

| TGC | ATG | GAT | TAT | GCA | GTG | ATC | CTC | GCA | AGA | CAA | GCT | GGA | GAG | ATG | ATT | 48 |
|---|---|---|---|---|---|---|---|---|---|---|---|---|---|---|---|---|
| Cys | Met | Asp | Tyr | Ala | Val | Ile | Leu | Ala | Arg | Gln | Ala | Gly | Glu | Met | Ile | |
| 1 | | | | 5 | | | | | 10 | | | | | 15 | | |

| CGA | GTT | GCT | CTA | AAA | AAT | AAG | ATG | GAT | GTC | ATG | ATT | AAA | AGT | TCT | CCA | 96 |
|---|---|---|---|---|---|---|---|---|---|---|---|---|---|---|---|---|
| Arg | Val | Ala | Leu | Lys | Asn | Lys | Met | Asp | Val | Met | Ile | Lys | Ser | Ser | Pro | |
| | | | 20 | | | | | 25 | | | | | 30 | | | |

| GCC | GAC | TTG | GTA | ACA | GTT | ACT | GAC | CAA | AAA | GTT | GAA | AAA | ATG | CTT | ATG | 144 |
|---|---|---|---|---|---|---|---|---|---|---|---|---|---|---|---|---|
| Ala | Asp | Leu | Val | Thr | Val | Thr | Asp | Gln | Lys | Val | Glu | Lys | Met | Leu | Met | |
| | | 35 | | | | | 40 | | | | | 45 | | | | |

| TCT | TCT | ATA | AAG | GAA | AAA | TAC | CCA | TAT | CAC | AGT | TTC | ATT | GGT | GAA | GAA | 192 |
|---|---|---|---|---|---|---|---|---|---|---|---|---|---|---|---|---|
| Ser | Ser | Ile | Lys | Glu | Lys | Tyr | Pro | Tyr | His | Ser | Phe | Ile | Gly | Glu | Glu | |
| 50 | | | | | 55 | | | | | 60 | | | | | | |

| TCT | GTG | GCA | GCC | GGG | GAA | AAG | ACA | GTC | TTC | ACA | GAG | CAG | CCC | ACG | TGG | 240 |
|---|---|---|---|---|---|---|---|---|---|---|---|---|---|---|---|---|
| Ser | Val | Ala | Ala | Gly | Glu | Lys | Thr | Val | Phe | Thr | Glu | Gln | Pro | Thr | Trp | |
| 65 | | | | 70 | | | | | 75 | | | | | 80 | | |

| ATC | ATT | GAT | CCC | ATT | GAC | GGG | ACG | ACC | AAC | TTT | GTG | CAC | CGG | TTT | CCC | 288 |
|---|---|---|---|---|---|---|---|---|---|---|---|---|---|---|---|---|
| Ile | Ile | Asp | Pro | Ile | Asp | Gly | Thr | Thr | Asn | Phe | Val | His | Arg | Phe | Pro | |
| | | | | 85 | | | | | 90 | | | | | 95 | | |

| TTT | GTA | GCT | GTT | TCG | ATT | GGC | TTC | GTT | GTA | AAT | AAA | GAG | ATG | GAG | TTT | 336 |
|---|---|---|---|---|---|---|---|---|---|---|---|---|---|---|---|---|
| Phe | Val | Ala | Val | Ser | Ile | Gly | Phe | Val | Val | Asn | Lys | Glu | Met | Glu | Phe | |
| | | | 100 | | | | | 105 | | | | | 110 | | | |

| GGA | GTT | GTA | TAC | AGC | TGT | GTG | GAA | GAT | AAG | ATG | TAT | ACG | GGC | AGG | AAA | 384 |
|---|---|---|---|---|---|---|---|---|---|---|---|---|---|---|---|---|
| Gly | Val | Val | Tyr | Ser | Cys | Val | Glu | Asp | Lys | Met | Tyr | Thr | Gly | Arg | Lys | |
| | | 115 | | | | | 120 | | | | | 125 | | | | |

| GGA | AAA | GGC | GCC | TTT | TGT | AAC | GGT | CAG | AAG | CTT | CGG | GTC | TCG | CAG | CAG | 432 |
|---|---|---|---|---|---|---|---|---|---|---|---|---|---|---|---|---|
| Gly | Lys | Gly | Ala | Phe | Cys | Asn | Gly | Gln | Lys | Leu | Arg | Val | Ser | Gln | Gln | |
| 130 | | | | | 135 | | | | | 140 | | | | | | |

| GAA | GAC | ATT | ACC | AAA | TCA | CTC | TTG | GTG | ACC | GAG | CTG | GGA | TCG | TCC | AGA | 480 |
|---|---|---|---|---|---|---|---|---|---|---|---|---|---|---|---|---|
| Glu | Asp | Ile | Thr | Lys | Ser | Leu | Leu | Val | Thr | Glu | Leu | Gly | Ser | Ser | Arg | |
| 145 | | | | | 150 | | | | | 155 | | | | | 160 | |

| AAG | CCG | GAG | ACT | TTG | CGG | ATT | GTT | CTC | TCC | AAC | ATG | GAA | AGG | CTT | TGC | 528 |
|---|---|---|---|---|---|---|---|---|---|---|---|---|---|---|---|---|
| Lys | Pro | Glu | Thr | Leu | Arg | Ile | Val | Leu | Ser | Asn | Met | Glu | Arg | Leu | Cys | |
| | | | | 165 | | | | | 170 | | | | | 175 | | |

| TCC | ATT | CCT | ATC | CAT | GGA | ATC | CGG | AGT | GTT | GGG | ACA | GCG | GCT | GTT | AAT | 576 |
|---|---|---|---|---|---|---|---|---|---|---|---|---|---|---|---|---|
| Ser | Ile | Pro | Ile | His | Gly | Ile | Arg | Ser | Val | Gly | Thr | Ala | Ala | Val | Asn | |
| | | | 180 | | | | | 185 | | | | | 190 | | | |

| ATG | TGC | CTT | GTG | GCA | ACG | GGA | GGA | GCG | GAT | GCC | TAT | TAC | GAG | ATG | GGG | 624 |
|---|---|---|---|---|---|---|---|---|---|---|---|---|---|---|---|---|
| Met | Cys | Leu | Val | Ala | Thr | Gly | Gly | Ala | Asp | Ala | Tyr | Tyr | Glu | Met | Gly | |
| | | 195 | | | | | 200 | | | | | 205 | | | | |

| ATC | CAC | TGC | TGG | GAC | ATG | GCT | GGA | GCT | GGC | ATC | ATC | GTC | ATA | GAG | GCT | 672 |
|---|---|---|---|---|---|---|---|---|---|---|---|---|---|---|---|---|
| Ile | His | Cys | Trp | Asp | Met | Ala | Gly | Ala | Gly | Ile | Ile | Val | Ile | Glu | Ala | |
| 210 | | | | | 215 | | | | | 220 | | | | | | |

| GGC | GGA | GTG | CTG | CTG | GAT | GTG | ACA | GGT | GGA | CCA | TTC | GAT | TTG | ATG | TCT | 720 |
|---|---|---|---|---|---|---|---|---|---|---|---|---|---|---|---|---|
| Gly | Gly | Val | Leu | Leu | Asp | Val | Thr | Gly | Gly | Pro | Phe | Asp | Leu | Met | Ser | |
| 225 | | | | | 230 | | | | | 235 | | | | | 240 | |

```
CGG AGA ATA ATT GCT GCA AGT AAT ATA GCA TTA GCA GAA AGA ATA GCC      768
Arg Arg Ile Ile Ala Ala Ser Asn Ile Ala Leu Ala Glu Arg Ile Ala
            245                 250                 255

AAA GAA CTT GAG ATA ATA CCT TTA CAA CGA GAC GAC GAA AGT TAGGCACGTA   820
Lys Glu Leu Glu Ile Ile Pro Leu Gln Arg Asp Asp Glu Ser
        260                 265                 270

GAACCGCATC CAGCTCCGTC ACACCTGCTC TCCCTGGGAT GTTTAAAGAT GTATGATGTC    880

ACTGATTTAA ATTAACTTT GCAGTCCTG                                       909
```

( 2 ) INFORMATION FOR SEQ ID NO: 4:

( i ) SEQUENCE CHARACTERISTICS:
    ( A ) LENGTH: 270 amino acids
    ( B ) TYPE: amino acid
    ( D ) TOPOLOGY: linear ( i i ) MOLECULE TYPE: protein ( x i ) SEQUENCE DESCRIPTION: SEQ ID NO: 4:

```
Cys Met Asp Tyr Ala Val Ile Leu Ala Arg Gln Ala Gly Glu Met Ile
 1           5                  10                  15

Arg Val Ala Leu Lys Asn Lys Met Asp Val Met Ile Lys Ser Ser Pro
            20                  25                  30

Ala Asp Leu Val Thr Val Thr Asp Gln Lys Val Glu Lys Met Leu Met
            35                  40                  45

Ser Ser Ile Lys Glu Lys Tyr Pro Tyr His Ser Phe Ile Gly Glu Glu
        50                  55                  60

Ser Val Ala Ala Gly Glu Lys Thr Val Phe Thr Glu Gln Pro Thr Trp
65                  70                  75                  80

Ile Ile Asp Pro Ile Asp Gly Thr Thr Asn Phe Val His Arg Phe Pro
                85                  90                  95

Phe Val Ala Val Ser Ile Gly Phe Val Val Asn Lys Glu Met Glu Phe
            100                 105                 110

Gly Val Val Tyr Ser Cys Val Glu Asp Lys Met Tyr Thr Gly Arg Lys
            115                 120                 125

Gly Lys Gly Ala Phe Cys Asn Gly Gln Lys Leu Arg Val Ser Gln Gln
        130                 135                 140

Glu Asp Ile Thr Lys Ser Leu Leu Val Thr Glu Leu Gly Ser Ser Arg
145                 150                 155                 160

Lys Pro Glu Thr Leu Arg Ile Val Leu Ser Asn Met Glu Arg Leu Cys
                165                 170                 175

Ser Ile Pro Ile His Gly Ile Arg Ser Val Gly Thr Ala Ala Val Asn
            180                 185                 190

Met Cys Leu Val Ala Thr Gly Gly Ala Asp Ala Tyr Tyr Glu Met Gly
            195                 200                 205

Ile His Cys Trp Asp Met Ala Gly Ala Gly Ile Ile Val Ile Glu Ala
        210                 215                 220

Gly Gly Val Leu Leu Asp Val Thr Gly Gly Pro Phe Asp Leu Met Ser
225                 230                 235                 240

Arg Arg Ile Ile Ala Ala Ser Asn Ile Ala Leu Ala Glu Arg Ile Ala
                245                 250                 255

Lys Glu Leu Glu Ile Ile Pro Leu Gln Arg Asp Asp Glu Ser
            260                 265                 270
```

( 2 ) INFORMATION FOR SEQ ID NO: 5:

( i ) SEQUENCE CHARACTERISTICS:

-continued

```
( A ) LENGTH: 28 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO: 5:

AATATTTTCA GCATATGGCT GATCCTTG                                    28

( 2 ) INFORMATION FOR SEQ ID NO: 6:

( i ) SEQUENCE CHARACTERISTICS:
                ( A ) LENGTH: 29 base pairs
                ( B ) TYPE: nucleic acid
                ( C ) STRANDEDNESS: single
                ( D ) TOPOLOGY: linear ( i i ) MOLECULE TYPE: cDNA ( x i ) SEQUENCE DESCRIPTION: SEQ ID NO: 6:

ATGACTATGA GCTGCAGTAA TTAATCTTC                                    29
```